(12) United States Patent
Weiss et al.

(10) Patent No.: US 9,316,608 B2
(45) Date of Patent: Apr. 19, 2016

(54) METHOD AND APPARATUS FOR TARGET DETECTION USING ELECTRODE-BOUND VIRUSES

(71) Applicant: THE REGENTS OF THE UNIVERSITY OF CALIFORNIA, Oakland, CA (US)

(72) Inventors: Gregory A. Weiss, Irvine, CA (US); Reginald M. Penner, Newport Beach, CA (US); Phillip Y. Tam, El Monte, CA (US); Li-Mei Yang, Fountain Valley, CA (US); Tyler Brigham, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 214 days.

(21) Appl. No.: 13/941,231

(22) Filed: Jul. 12, 2013

(65) Prior Publication Data

US 2014/0014536 A1 Jan. 16, 2014

Related U.S. Application Data

(62) Division of application No. 12/282,143, filed as application No. PCT/US2007/063723 on Mar. 9, 2007, now Pat. No. 8,513,001.

(60) Provisional application No. 60/743,448, filed on Mar. 9, 2006.

(51) Int. Cl.
*G01N 27/327* (2006.01)

(52) U.S. Cl.
CPC .......... *G01N 27/327* (2013.01); *G01N 27/3277* (2013.01)

(58) Field of Classification Search
CPC .......................... G01N 27/327; G01N 27/3277
See application file for complete search history.

(56) References Cited

U.S. PATENT DOCUMENTS

2002/0090649 A1 7/2002 Chan et al.
2002/0098531 A1 7/2002 Thacker
(Continued)

OTHER PUBLICATIONS

Brett, A.M. Oliveira, et al., Synthetic Oligonucleotides: AFM characterisation and electroanalytical studies, Bioelectrochemistry, 67, pp. 181-190 (2005).
(Continued)

*Primary Examiner* — Melanie Y Brown
(74) *Attorney, Agent, or Firm* — Vista IP Law Group LLP

(57) ABSTRACT

A biosensor that is capable of detecting the presence and/or concentration of an analyte or biomarker includes at least one electrically conductive electrode operatively coupled to an impedance analyzer for measuring the change in the resistive impedance $\Delta Z_{Re}$ of the electrode in response to an applied alternating current at a plurality of frequencies. In one embodiment, at least one electrode is covered with a self-assembled monolayer that is chemically bonded to a surface. A plurality of virus particles such as phage viruses are immobilized on the self-assembled monolayer and may be exposed to a test or sample solution. The virus particles may be obtained from phage-displayed libraries to detect a wide variety of targets including, for example, DNA, RNA, small molecules, and proteins or polypeptides. In another embodiment, the virus particles are electrostatically bound to a substrate in between a pair of elongated electrodes disposed on a substrate.

13 Claims, 13 Drawing Sheets

(56) References Cited

U.S. PATENT DOCUMENTS

| | | | |
|---|---|---|---|
| 2003/0194400 A1 | 10/2003 | Liu et al. | |
| 2004/0005540 A1* | 1/2004 | Petrenko et al. | 435/5 |
| 2004/0137430 A1 | 7/2004 | Anderson et al. | |
| 2005/0059105 A1* | 3/2005 | Alocilja et al. | 435/7.32 |
| 2005/0208592 A1* | 9/2005 | Caron | G01N 33/54373 435/7.1 |
| 2006/0011493 A1* | 1/2006 | Kontschieder et al. | 205/792 |
| 2006/0160100 A1* | 7/2006 | Gao et al. | 435/6 |
| 2007/0242111 A1* | 10/2007 | Pamula et al. | 347/81 |
| 2008/0193418 A1* | 8/2008 | Walter | A61K 51/1203 424/93.6 |

OTHER PUBLICATIONS

Olsen, Eric V., et al., Affinity-selected filamentous bacteriophage as a probe for acoustic wave biodetectors of *Salmonella typhimurium*, Biosensors and Bioelectronics, 21, pp. 1434-1442 (2006).

Yang, Li-Mei, et al., Virus Electrodes for Universal Biodetection, Analytical Chemistry, 78, pp. 3265-3270 (2006).

PCT International Search Report for PCT/US2007/063723, Applicant: The Regents of the University of California, Form PCT/ISA/210 and 220, dated Aug. 14, 2008 (6 pages).

PCT Written Opinion of the International Search Authority for PCT/US2007/063723, Applicant: The Regents of the University of California, Form PCT/ISA/237, dated Aug. 14, 2008 (5 pages).

PCT International Preliminary Report on Patentability (Chapter I of the Patent Cooperation Treaty) for PCT/US2007/063723, Applicant: The Regents of the University of California, Form PCT/IB/326 and 373, dated Oct. 9, 2008 (7 pages).

Supplementary European Search Report for European Patent Application No. 07758285.6-2204 (PCT/US2007063723), Applicant: The Regents of the University of California, dated Mar. 27, 2012 (6 pages).

Decker, Jochen et al., Characterization of a human pancreatic secretory trypsin inhibitor mutant binding to *Legionella pneumophila* as determined by a quartz crystal microbalance, Journal of Immunological Methods, 233 (2000) 159-165.

Goldman, Ellen R. et al., Phage-displayed peptides as biosensor reagents, Journal of Molecular Recognition, 2000, 13:382-387.

Yang, Li-Mei C. et al., Virus Electrodes for Universal Biodetection, Anal. Chem., 2006, 78, 3265-3270.

Canadian Patent Office Communication dated May 29, 2013 in Canadian Patent Application No. 2,646,987, Applicant: The Regents of the University of California (3pages).

Canadian Patent Office Communication dated Jan. 2, 2014 in Canadian Patent Application No. 2,646,987, Applicant: The Regents of the University of California (2pages).

Canadian Patent Office Notice of Allowance dated Jun. 12, 2014 in Canadian Patent Application No. 2,646,987, Applicant: The Regents of the University of California (1page).

European Patent Office Communication dated Aug. 7, 2013 in European Patent Application No. 07758285.6-1554, Applicant: The Regents of the University of California (4pages).

European Patent Office Communication dated Feb. 19, 2015 in European Patent Application No. 07758285.6-1554, Applicant: The Regents of the University of California (5pages).

* cited by examiner

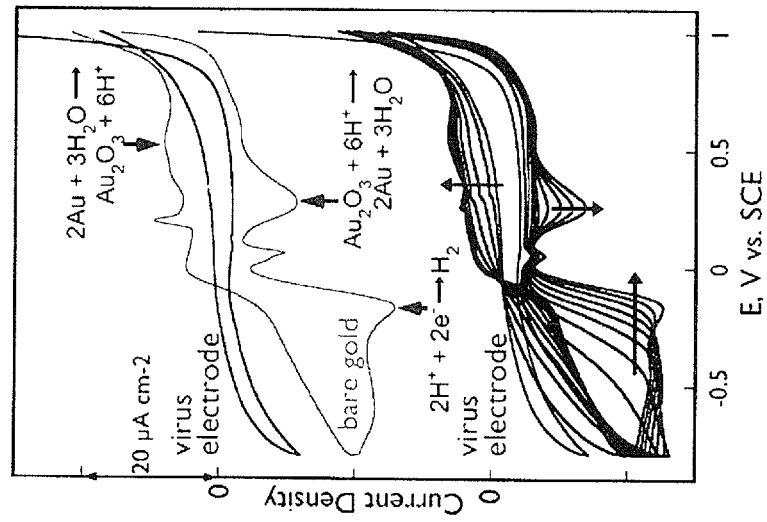
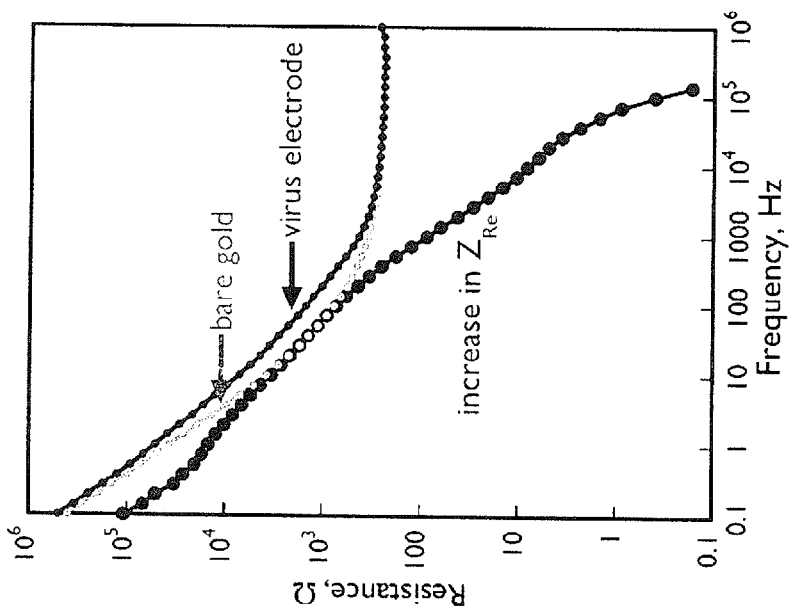
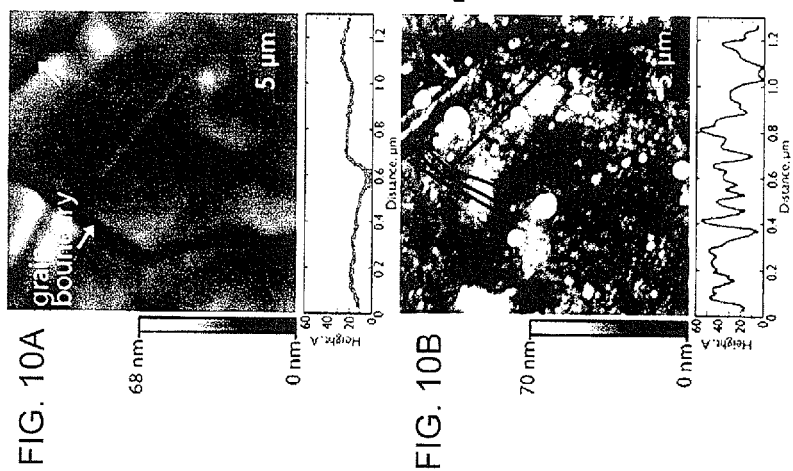
FIG. 10A  FIG. 10B  FIG. 10C  FIG. 10D

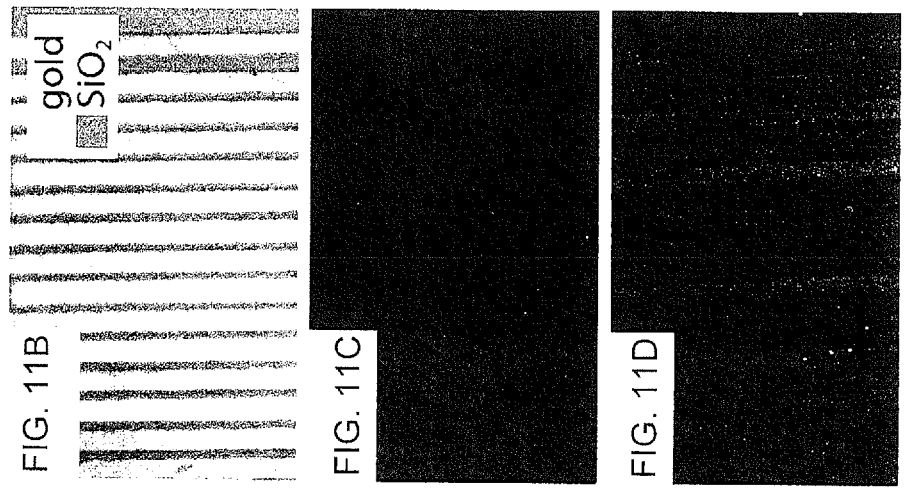
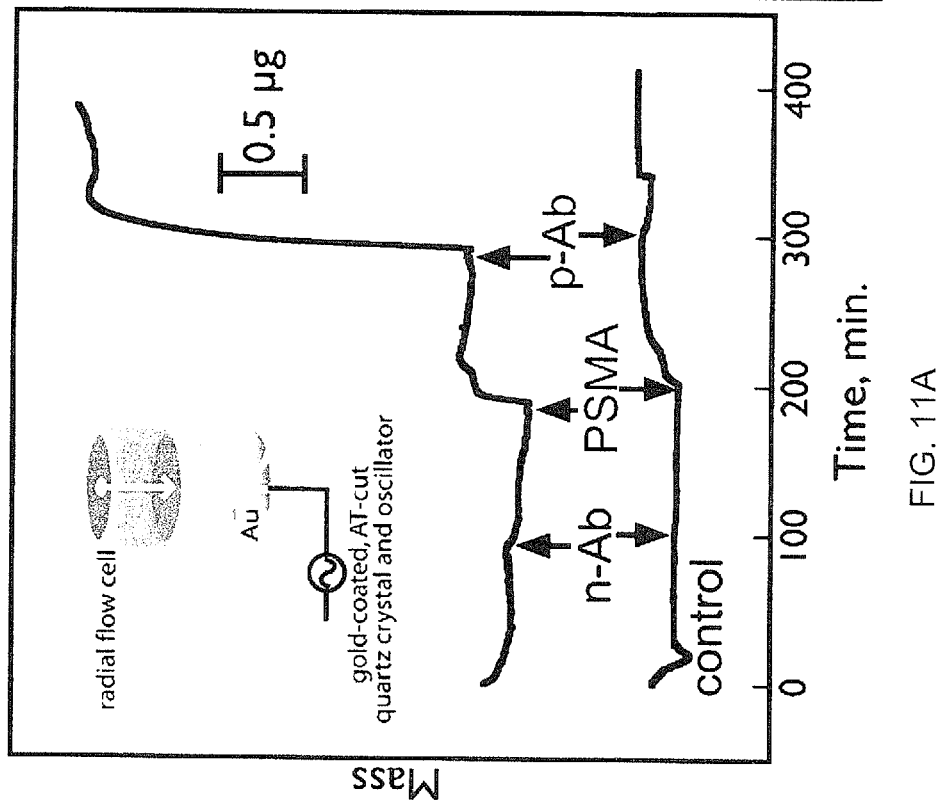
FIG. 11A
FIG. 11B
FIG. 11C
FIG. 11D

METHOD AND APPARATUS FOR TARGET DETECTION USING ELECTRODE-BOUND VIRUSES

REFERENCE TO RELATED APPLICATIONS

This application is a divisional of U.S. patent application Ser. No. 12/282,143 filed on Sep. 8, 2008, now issued at U.S. Pat. No. 8,513,001, which itself is a U.S. National Stage filing under 35 U.S.C. §371 of International Application No. PCT/US2007/063723, filed Mar. 9, 2007, which claims priority of U.S. Provisional Patent Application No. 60/743,448 filed on Mar. 9, 2006. The contents of the aforementioned applications are hereby incorporated herein by reference in their entirely. Priority to the aforementioned applications is hereby expressly claimed in accordance with 35 U.S.C. §§119, 120, 365 and 371 and any other applicable statutes.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Grant Nos. EF-0404057 and CHE-0111557 awarded by the National Science Foundation (NSF).

FIELD OF THE INVENTION

The field of the invention generally relates to sensors. More particularly, the field of the invention pertains to a electrochemical-based biosensors that detect analyte binding to viruses that are adhered or bonded to an electrode surface.

BACKGROUND

There is a growing need for devices and methods that can detect biomarkers and other chemical or organic species within a sample. For example, many disease states may be diagnosed or their progression monitored by the detection of one or more biomarkers. For example, a test for prostate cancer may rely on the level of prostate-specific antigen (PSA) present in a sample. In still other contexts, such as biowarfare and biodefense applications, there is a growing need for relatively small, sensitive devices that are able to quickly detect the presence of small quantities of harmful agents within the environment.

Phage-displayed peptide libraries have been investigated as a potential tool that could offer the ability to test or screen for a large number of target molecules. For example, phage-displayed peptide libraries having on the order of $10^{10}$ unique members offer the promise of universal biorecognition. Unfortunately, this technology has found only limited application in biosensors. In prior work, detecting molecular recognition between phage and target has focused on a "sandwich assay" scheme involving the detection of phage binding to immobilized target using rather complicated and expensive testing equipment such as quartz crystal microbalances, microelectrode arrays, nanowire field effect transistors, bead-based electrochemical immunoassays, electric DNA chips, and fluoroimmunoassays. Still other techniques have been proposed for the rapid detection of, for example, bacteria using a phagemid electrochemical assay system. Still others have proposed using affinity-selected filamentous bacteriophage that is immobilized to piezoelectric transducers. In this last scheme, specific bacterial binding purportedly results in resonance frequency changes.

There thus is a need for a device and method that avoids the problems associated with prior sandwich-based assays. Such a system should be amenable to miniaturization and have a rapid response time.

SUMMARY

In a first aspect of the invention, a sensor device that may take the form of a biosensor includes at least one electrode that is operatively connected to an impedance analyzer able to measure the change in resistive impedance $\Delta Z_{Re}$ of the electrode in response to an applied alternating current over a range of frequencies. The electrode itself is electrically conductive and coated or bonded with a self-assembled monolayer (SAM). For example, the SAM may include N-hydroxysuccinimide thioctic ester that reacts with an electrically-activated electrode (e.g., gold) to form a thiol-gold bonded SAM. The virus is then adhered to the SAM through, for example, covalent bonding. For instance, in the case of bacteriophage virus, the phage may be covalently tethered to the SAM through the formation of amide bonds between free amines of the phage and the activated carboxylate. Optionally, gaps in the SAM and un-reacted NHS esters may be filled or capped with a macromolecule such as bovine serum albumin (BSA).

The virus (e.g., phage) can be selected to bind with any number of targets including, for example, small molecules, nucleic acids, proteins, and peptides. The impedance analyzer takes electrochemical impedance spectrographic measurements of the electrode in the un-bound and bound states and calculates a change in the resistive impedance $\Delta Z_{Re}$. The change in the resistive impedance $\Delta Z_{Re}$ over a range of applied frequencies is monitored and used to determine the presence (or absence) of the target within a sample solution. In addition, the concentration of the target (e.g., analyte or biomarker) may be determined if the change in the resistive impedance $\Delta Z_{Re}$ is compared with a calibration curve. It has been found that good or favorable signal-to-noise (S/N) ratios (e.g., >10) can be obtained over a broad range of applied frequencies from about 2 kHz to about 500 kHz.

In another embodiment of the invention a biosensor includes an electrically conductive electrode operatively coupled to an impedance analyzer for measuring the change in the resistive impedance $\Delta Z_{Re}$ of the electrode when bound to a target or analyte as compared to the resistive impedance $\Delta Z_{Re}$ of the electrode in a non-bound (i.e., control) state. A self-assembled monolayer is chemically bonded to the surface of the electrically conductive electrode. For example, the electrode may comprise a gold electrode formed from a biologically inert element such as gold or platinum. A plurality of virus particles are bound to the self-assembled monolayer. The bonding may include, for example, a covalent bond. In one aspect, the virus particles comprise phage particles selected from a phage-displayed library that are selective to one or more targets.

In another embodiment of the invention, a method of forming a sensor includes providing at least one electrically conductive electrode and bonding a self-assembled monolayer to the at least one electrically conductive electrode. A plurality of virus particles are then bound or adhered to the self-assembled monolayer. At least one electrode is operatively connected to an impedance analyzer for measuring the change in resistive impedance $\Delta Z_{Re}$ of the conductive electrode in response to an applied alternating current over a range of frequencies.

In another embodiment of the invention, a method for detecting an analyte in a test or sample solution includes providing a sensor comprising at least one electrically conductive electrode having a self-assembled monolayer bonded thereto and a plurality of virus particles chemically bound to the self-assembled monolayer. At least one electrically conductive electrode is operatively connected to an impedance measurement device. The sensor is then exposed to the test solution. The change in the resistive impedance $\Delta Z_{Re}$ of the electrically conductive electrode(s) is measured and the presence of the analyte is detected based at least in part on the measured change in resistive impedance $\Delta Z_{Re}$ of the electrically conductive electrode. Here, the change in resistive impedance $\Delta Z_{Re}$ includes taking the difference of the measured resistive impedance $Z_{Re}$ of the electrically conductive electrode when bound to the analyte as compared to when the electrically conductive electrode is not bound to the analyte, for example, the at least one electrically conductive electrode is in the test solution (e.g., buffer solution).

In still another aspect of the invention, a sensor includes a substrate and a plurality of electrode lines disposed on the substrate, each electrode line being operatively coupled to an impedance analyzer for measuring the change in the resistive impedance $\Delta Z_{Re}$ of electrode line(s) after exposure to target (s). For example, each electrode may be scanned or addressed using off-board switching circuitry. An insulative layer is disposed over each of the plurality of electrode lines, wherein an opening is formed between adjacent insulative layers. A plurality of virus particles are adhered to the surface of the substrate in the opening regions formed between adjacent insulative layers. In one aspect, the plurality of virus particles may be different in each opening thereby permitting the sensor to detect and optionally measure the concentration of multiple different targets or analytes in a test solution that is placed on or flowed over the substrate. The sensor may be integrated into a flow cell for monitoring a flow of test solution or may be used in a batch process.

BRIEF DESCRIPTION OF THE DRAWINGS

FIG. 10A illustrates an atomic force microscope (AFM) image of flame-annealed gold surface on quartz.

FIG. 10B illustrates an AFM image of a similar gold electrode after covalent attachment of phage particles.

FIG. 10C is a graph of the electrode resistance $Z_{Re}$ as a function of frequency. Plots are shown for a bare gold electrode as well as for the electrode after the covalent attachment of M13 phage and exposure of the surface with bovine serum albumin (BSA). Also shown on this graph is the increase in measured resistance relative to the "clean" gold electrode that results from the bound phage particles and BSA.

FIG. 10D illustrates several cyclic voltagrams at 20 mV s$^{-1}$ for a bare or "clean" gold electrode in phosphate buffered fluoride (PBF). Also illustrated is the cyclic voltagram for the phage-covered electrode following exposure to n-Ab and p-Ab lasting >8-10 hours in flowing buffer solution. Reactions characteristic of the exposed or "clean" gold electrode were suppressed by the covalently bound virus particles. As seen in FIG. 10D by the opposing arrows in the lowermost trace, this layer could be removed gradually by scanning the potential of the electrode to +1.0 V versus the saturated calomel electrode (SCE) revealing the voltammetric features of the underlying gold surface.

FIG. 11A illustrates a radial flow cell-based electrode device that utilized QCM measurements of mass versus time showing the exposure of the virus electrode to n-Ab, PSMA, and p-Ab.

FIG. 11B illustrates a photomicrograph of gold electrodes patterned on silicon after the formation of a covalent virus surface.

FIG. 11C illustrates a fluorescence micrograph of patterned gold electrodes exposed to thioctyl NHS ester followed by consecutive incubation in buffer, BSA, then fluorescin-labeled p-Ab. Here, M13 phage was omitted and, as a result, no binding to the electrode is observed.

FIG. 11D illustrates a fluorescence micrograph after attachment of the M13 phage to the thioctyl self-assembled monolayer and binding of fluorescin-labeled p-Ab.

DETAILED DESCRIPTION

Figure 1:
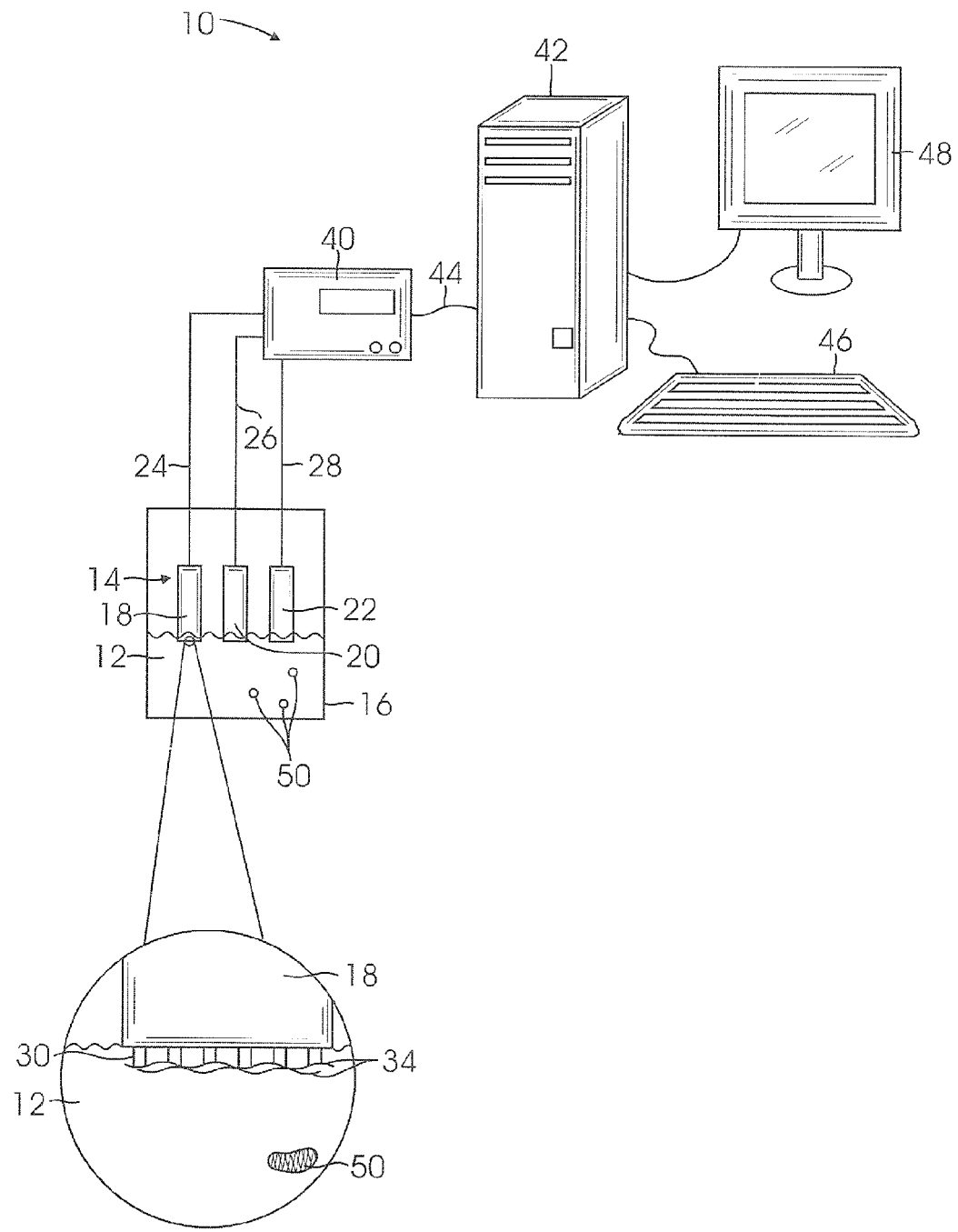
FIG. 1 illustrates a schematic view of a system for measuring the presence of or concentration of a target or analyte according to one embodiment.
Figure 3:
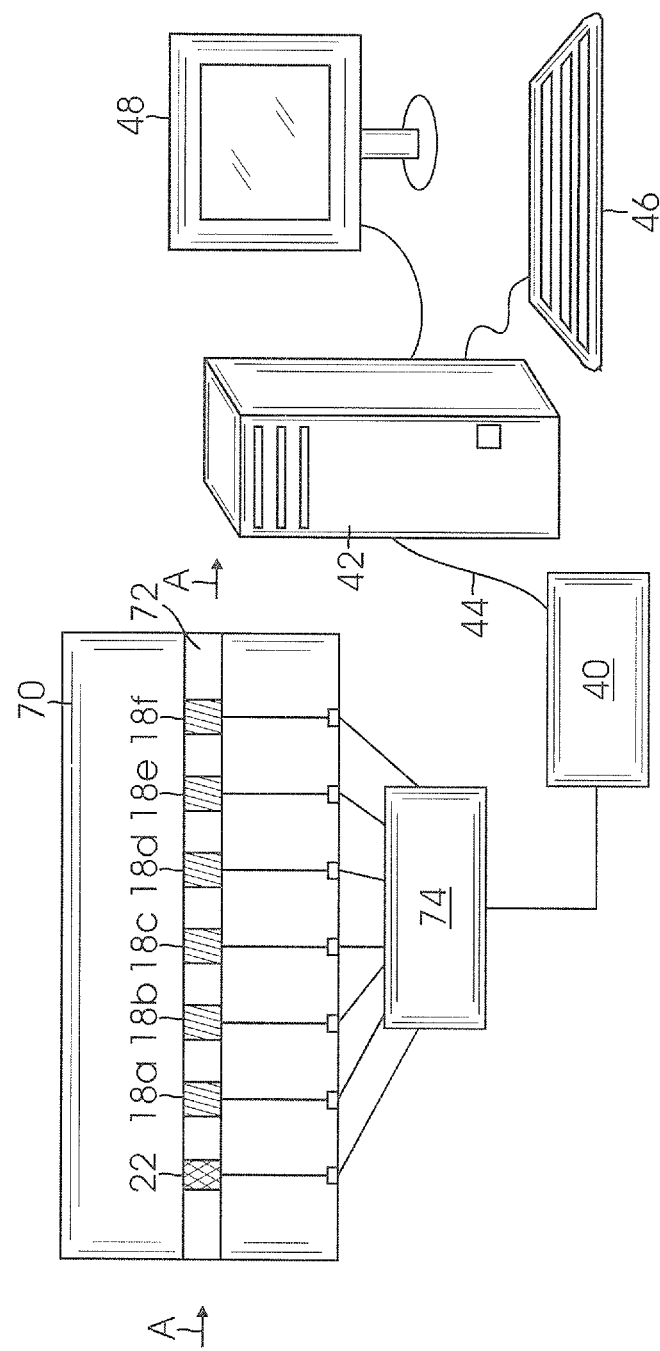
FIG. 3 illustrates a microfluidic based system that incorporates a plurality of measurement electrodes. The microfluidic based system includes switching circuitry for sampling the plurality of electrodes.

FIG. 1 illustrates a system 10 according to one embodiment of the invention for detecting and/or measuring the concentration of an analyte or target 50 contained in a sample solution 12 using a sensor 14. As used herein, analyte or target refers to any number of materials that may be bound to the sensor 14. This includes by way of example, nucleic acids (e.g., DNA, RNA), small molecules, peptides, polypeptides, proteins, enzymes, single-celled organisms (e.g., bacteria, algae, viruses), tissue samples, and the like. The sample solution 12 may include an aqueous-based solution having one or more ionic species therein. The solution 12 may include a biological-based solution or component (e.g., blood or urine) or may be obtained from the environment or from a manufacturing process. The solution 12 may be held within in a container 16 such as a vial, cuvette, or other holder such that illustrated in FIG. 1. In this regard, measurements made using the system 10 are performed in a batch process. Alternatively, as illustrated in FIG. 3, the system 10 may also be used in flow-based systems. For example, sample solution 12 may flow over the sensor 14 thereby permitting the detection and/or the measurement of the concentration of an analyte or target in a continuous or semi-continuous flow operation. For example, the sensor 14 may be integrated into a process stream of a manufacturing operation to detect for the presence of a contaminant or toxin.

Referring back to FIG. 1, the sensor 14 includes a working electrode 18, a reference electrode 20, and a counter electrode 22. During operation of the system 10, as described in more detail below, electrons flow between the working electrode 18 and the counter electrode 22. In some embodiments, the reference electrode 20 may be omitted entirely. The working electrode 18 is formed from an electrically conductive metal such as, for instance, gold. The portion(s) of the working electrode 18 that will be in contact with the solution 12 are covered with a self-assembled monolayer (SAM) 30. For example, in the context of a gold working electrode 18, the SAM 30 may be formed by exposing the bare gold working electrode 18 to N-hydroxysuccinimide thioctic ester. The working electrode 18 further includes a plurality of viruses or virus particles 34 that are chemically bound to the SAM 30. In another embodiment, electrical impedance measurements may be made using a two electrode configuration in which the working electrode 18 and sense electrode 24 are combined into one electrode and the reference electrode 20 and the counter electrode 22 are combined into the second electrode. FIG. 6B illustrates this configuration with a sensor 90 but it may also be used in connection with sensor 14.

In one preferred embodiment, the virus particles 34 comprise unique phage particles 34 that are selected from phage-displayed libraries. In this regard, the sensor 14 can be tailored such that the virus particles 34 selectively binds the target(s) 50 of interest. By selecting the appropriate virus 34, the sensor 14 may be tailored to the particular application. For example, virus particles 34 may be selected that bind to a particular protein or polypeptide that is indicative of the presence of an infectious agent. For example, the target 50 may include anthrax lethal factor, vaccinia (smallpox vaccine), francisella tularemia, cholera toxin, botulinum toxin, SARS S protein, and the like. In this regard, the sensor 14 may be particularly suited for biodefense applications.

The target 50 may also include a protein or biological marker indicative of a disease state. For example, as described herein, the target 50 may include prostate specific membrane antigen (PSMA) which is a marker indicative of prostate cancer. The target 50 may also include any number of cell signaling proteins that may be used to detect and monitor any number of diseases. The target 50 may also include a drug (e.g., human growth factor) or drug metabolite such that the sensor 14 may be used in drug detection applications.

Figure 5:
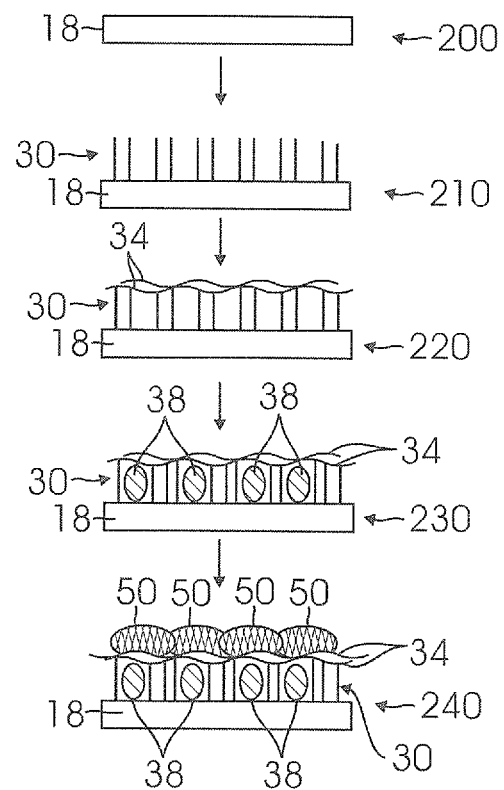
FIG. 5 illustrates a process of forming a sensor according to one aspect of the invention.

Still referring to FIG. 1, the SAM 30 preferably completely coats the portion(s) of the working electrode 18 that will contact the sample solution 12. If there any holes or openings in the SAM 30 this will lead to loss or swamping of the signal when the target of interest 50 binds to the virus particles 34. Because of this, during formation of the complete sensor 14, it is desirable to add a macromolecule 38 (as shown in FIG. 5) to fill in any holes or gaps within the SAM 30. Of course, there may be other SAMs 30 where the use of one or more macromolecules 38 is unnecessary.

As seen in FIG. 1, the sensor 14 includes a counter electrode 22. The counter electrode 22 may include, for example, an electrically conductive metal such as platinum. FIG. 1 also illustrates a sensor 14 that includes a reference electrode 20. The reference electrode 20 may include, for example, a saturated calomel electrode (SCE). Of course, in other embodiments, the reference electrode 20 may be omitted entirely. In the embodiment of FIG. 1, the working electrode 18, reference electrode 20, and counter electrode 22 are coupled via respective signal lines or conductors 24, 26, 28 to an impedance analyzer 40. The impedance analyzer 40 may also include a four electrode configuration that includes a working electrode 18, a reference electrode 20, a counter electrode 22, and a sensing electrode 24 (as shown in FIG. 6B).

The impedance analyzer 40 includes the ability to apply an alternating current to the working electrode 18 over a variety of frequencies. In addition, the amplitude of the applied electrical current may be adjusted. The impedance analyzer 40 may include any number of frequency response analyzers, potentiostats, and galvanostats. For example, the PARSTAT 2263 available from Princeton Applied Research, Oak Ridge, Tenn. may be used in connection with the sensor 14. The PARSTAT 2263 is capable of making impedance measurements within the frequency range of 10 µHz to 1 MHz. The impedance analyzer 40, either alone or in combination with software loaded onto an associated PC (discussed below), is able to measure the resistive impedance $Z_{Re}$ of the working electrode 18. In addition, the impedance analyzer 40 (or associated software) is also capable of calculating the change in the resistive impedance $\Delta Z_{Re}$ of the working electrode 18. For example, $\Delta Z_{Re}$ may be calculated as a difference between the measured resistive impedance $Z_{Re}$ when targets 50 are bound to the virus particles 34 on the working electrode 18 as compared to the measured resistive impedance $Z_{Re}$ of the working electrode 18 in the solution 12 (e.g., buffered solution) without the presence of the targets 50. In yet another alternative, the impedance analyzer 40 along with the software (e.g., computational algorithms) for determining the resistive impedance $Z_{Re}$ of the working electrode 18 and the changes in the resistive impedance $\Delta Z_{Re}$ may be integrated into one or more custom-built processors such as ASIC(s). This would decrease the overall size of the system and also reduce the cost of the device.

As seen in FIG. 1, the impedance analyzer 40 may interface with a computer 42 via communications interface 44. The interface 44 may include, for example, a USB cable or the like. The computer 42 may include a typically personal computer or PC that may include one or more input devices 46 like the illustrated keyboard along with a monitor 48 that can be used, for example, to display results. Of course other input devices 46 such as a mouse or the like may also be connected to the computer 42. Likewise the computer 42 may include a number of peripheral devices such as a printer (not shown) or the like. Preferably, the computer 42 operatively coupled to the impedance analyzer 40 contains software to control the impedance analyzer 40 as well as process and analyze the data produced during use. For example, for the PARSTAT 2263 system discussed above, the PowerSINE software available from Princeton Applied Research may be used for electrochemical impedance measurements.

Figure 2:
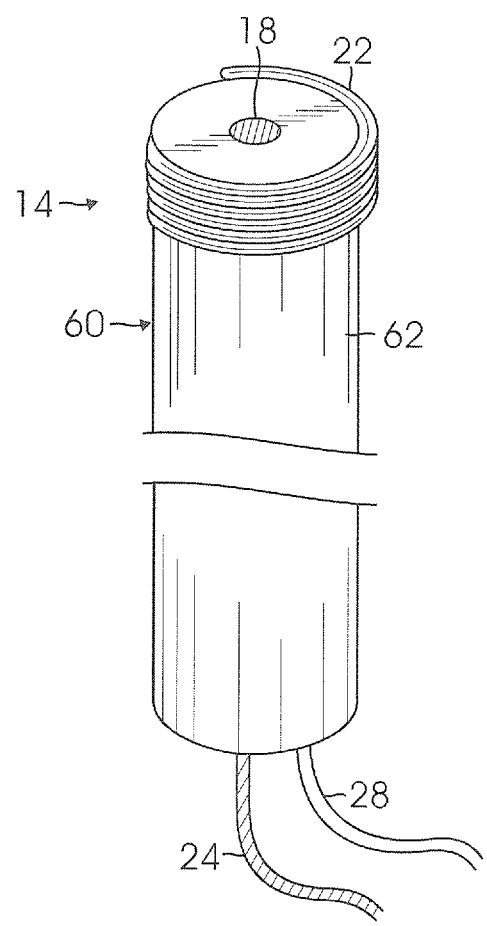
FIG. 2 illustrates a probe-based design of a sensor that uses a virus-bound electrode of the type described herein.

FIG. 2 illustrates an embodiment of a sensor 14 that is manufactured in the form of a probe 60. The probe 60 illustrated in FIG. 2 may be sized such that it can be manipulated by hand or robot and manually inserted into a test or sample solution 12. For example, the probe 60 may include an elongate body 62 that is made of an insulative material such as plastic or polyolefin. One end of the probe 60 includes the working electrode 18 which may comprise, for example, a gold electrode in the shape of a disk or the like (e.g., 3 mm in diameter). The counter electrode 22 may be formed by platinum wire which is wrapped around an exterior surface of the elongate body 62. Both the working electrode 18 and counter electrode 22 are electrically connected to wires or conductors 24, 28 that are adapted to connect to the impedance analyzer 40.

FIG. 3 illustrates another embodiment of a sensor 14 that is integrated into a microfluidic device 70. In this example, a plurality of working electrodes 18a, 18b, 18c, 18d, 18e, 18f along with a counter electrode 22 are positioned within a channel 72 of the microfluidic device 70. Sample fluid 12 flows down the channel 72 in the direction of arrows A. Each electrode 18a-18f, and 22 is electrically coupled to the impedance analyzer 40 via switching circuitry 74. The switching circuitry 74 permits the impedance analyzer 40 to scan each of the working electrodes 18a-18f. In one aspect of the invention, each working electrode 18a-18f includes a distinct virus 34 that is capable of binding to a specific target 50. For example, working electrode 18a may bind to anthrax lethal factor which working electrode 18b may bind to botulinum toxin. In this regard, a small microfluidic-based detection device may be created which can scan for any number of potential analytes or targets 50. Unlike the probe-based device of FIG. 2, this embodiment is particularly well suited for flow or non-batch processes where a stream of fluid is monitored for the presence of one or more analytes 50. Also, while the device of FIG. 3 has been described in terms a microfluidic-based device, the same sensor 14 may be integrated into larger, non-microfluidic-based flow devices.

Figure 4:
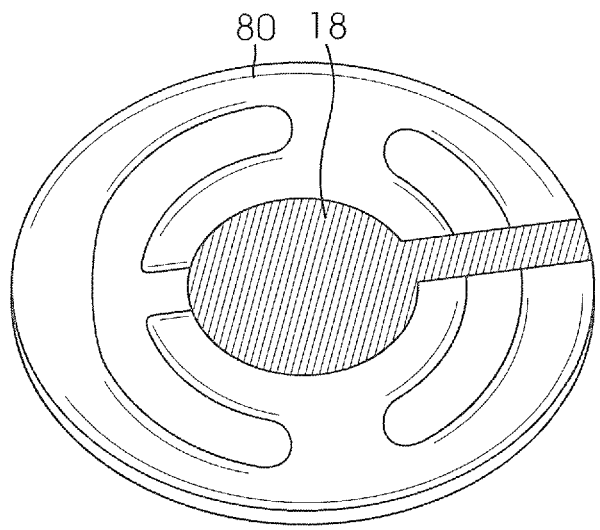
FIG. 4 is a perspective view of an electrode disposed on top of a QCM sensor according to one aspect of the invention.

FIG. 4 illustrates a working electrode 18 that is positioned atop a quartz crystal microbalance (QCM) sensor 80. The QCM sensor 80 permits the sensor 14 to take mass measurements in addition to measuring the resistive impedance $Z_{Re}$ as described herein. For example, the QCM 80 and working electrode 18 may be positioned at the end of the probe 60 illustrated in FIG. 2. The QCM 80 is particularly useful in sensor embodiments wherein the electrode 18 is reusable. For example, a washing solution along with an applied alternating current may be able to selectively remove the bound targets 50 from the working electrode 18 making the same reusable. The QCM sensor 80 may permit the monitoring of the accumulation and removal of the bound targets 50 during this process.

FIG. 5 illustrates a process of making a sensor 14 according to one embodiment of the invention. Initially, as seen in step 200 a metal working electrode 18 is provided. The metal working electrode 18 may comprise a gold electrode. The gold working electrode 18 may be polished and activated by electrochemically depositing a small layer of gold. Other non-chemical modalities may also be used to deposit a thin layer of activated gold on the electrode 18 (e.g., sputtering). Next, as seen in step 210, a self-assembled monolayer (SAM) 30 is grown on the working electrode 18. The SAM 30 may be formed by rinsing the sensor 14 in Nanopure water, drying the sensor 14 with Nitrogen and incubating the working electrode 18 in a solution containing N-hydroxysuccinimide thioctic ester dissolved in dimethylforamide (DMF). The electrode 18 should be incubated for several hours (e.g., at least eighteen hours). Generally, the SAM 30 has thickness on the order of several nanometers but the thickness could be less or more depending on the constituent of the SAM 30. Next, with reference to step 220 in FIG. 5, virus particles 34 are then bound to the SAM 30 by incubating the NHS-TE modified working electrode 18 in the phage solution. The solution may be shaken to aid the process. Next, in step 230, the virus-laden electrodes 18 may be washed with buffer solution and then with phosphate buffered fluoride (PBF). In order to fill in any gaps or holes in the SAM 30, the electrode 18 may be dipped into a solution containing a macromolecule 38. The macromolecule 38 may include BSA, ovalbumin, casein, or other large macromolecules. After exposure to the macromolecule 38, the virus/macromolecule-modified electrode 18 may be rinsed in a rinsing solution (e.g., Tween-20/PBF buffer) and then washed with a washing buffer. Step 240 illustrates the working electrode 18 after binding with a number of targets 50.

Figure 6A:
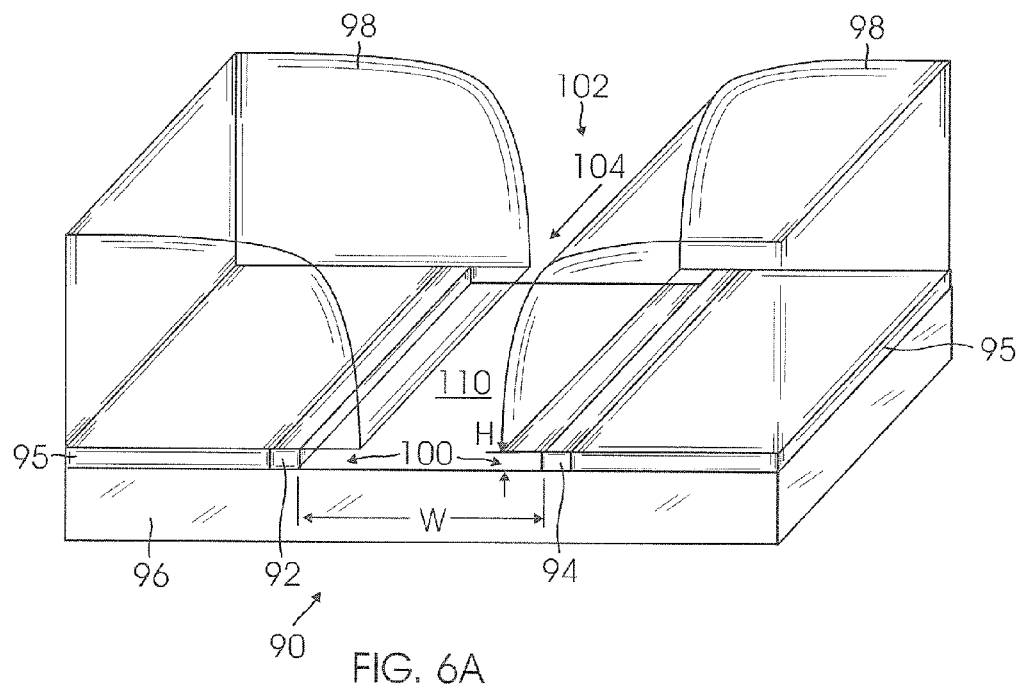
FIG. 6A illustrates a perspective view of a sensor according to another embodiment. In this embodiment electrode wires or lines are formed on top of a substrate. The electrode wires are covered by an insulating layer that includes an access pathway to the region of the substrate between adjacent electrode wires.
Figure 6B:
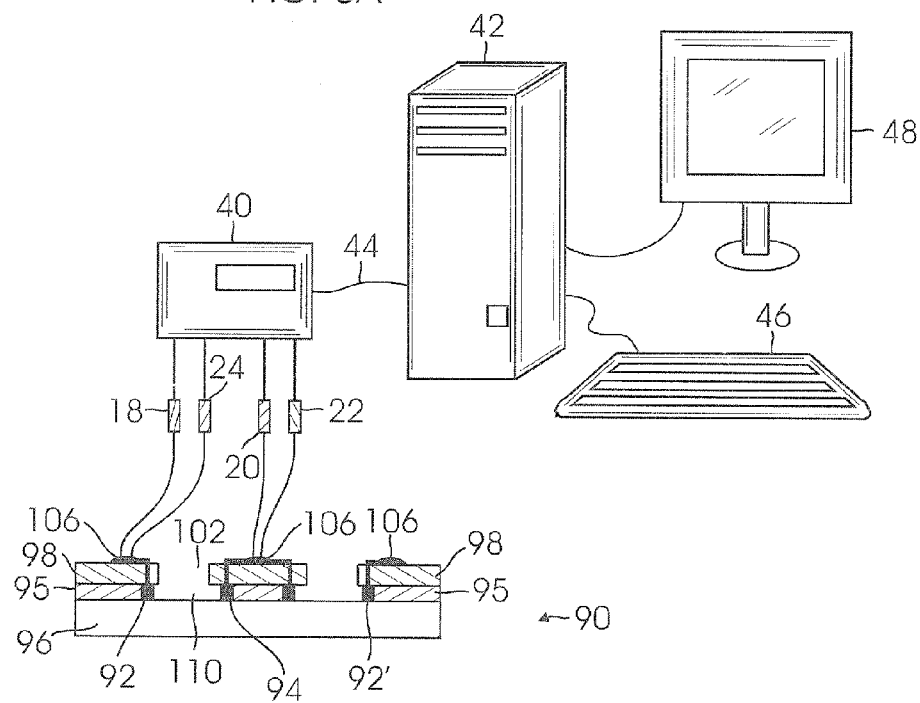
FIG. 6B illustrates an impedance analyzer coupled to the sensor of the type illustrated in FIG. 6A.

FIGS. 6A and 6B illustrate another embodiment of a sensor 90. In this embodiment, a plurality of elongate electrodes 92, 94 are formed on top of a substrate 96. The substrate 96 is preferably formed from an insulative material such as glass or oxidized silicon. The plurality of elongate electrodes 92, 94 may comprise micrometer or even nanometer-sized wires or lines that formed along an upper surface of the substrate 96. As seen in FIG. 6A, the elongate electrodes 92, 94 are located adjacent to a layer of nickel 95 and are formed from gold. During application of the alternating current, the electrical field is largely confined to the region 110 located just above the surface of the substrate 96. Each elongate electrode 92, 94 is located beneath an insulator layer 98. For example, the insulator layer 98 may comprise photoresist. In insulator layer 98 isolates or focuses the electrical field to the surface region just above the substrate 96. Importantly, this removes the bulk solution resistance from the resistive impedance measurements, thereby significantly increasing the sensitivity of the sensor 90. In one preferred aspect, the elongate electrodes 92, 94 are located beneath a recessed portion 100 of each insulator layer 98. This further aids in focusing the electrical field between the two electrodes 92, 94 at the surface of the substrate 96. As seen in FIGS. 6A and 6B, there is an opening 102 the insulator layer 98 that permits access to the surface region 100 located between the two electrodes 92, 94. The opening 102 creates a channel or valley 104 between adjacent electrodes 92, 94. The elongate electrodes 92, 94 may have a height (H) within the range of about 5-80 nm. In addition, the electrodes 92, 94 may be separated by a width (W) of approximately 10 µm to about 15 mm.

FIG. 6B illustrates an impedance analyzer 40 operatively coupled to the electrodes 92, 94 of the sensor 90. In this embodiment, the working electrode 18 and the sense electrode 24 are electrically connected to one electrode 92 while the reference electrode 20 and the counter electrode 22 are connected to the second electrode 94. Electrical contacts 106 may be formed on the surface of the insulator layer to provide electrical contact to the underlying elongate electrodes 92, 94. For example, the electrical contacts 106 may be formed from a metallic paint that is applied to a scored or cut surface of the insulator layer 98 that provides electrical contact to each electrode 92, 94.

Figure 7:
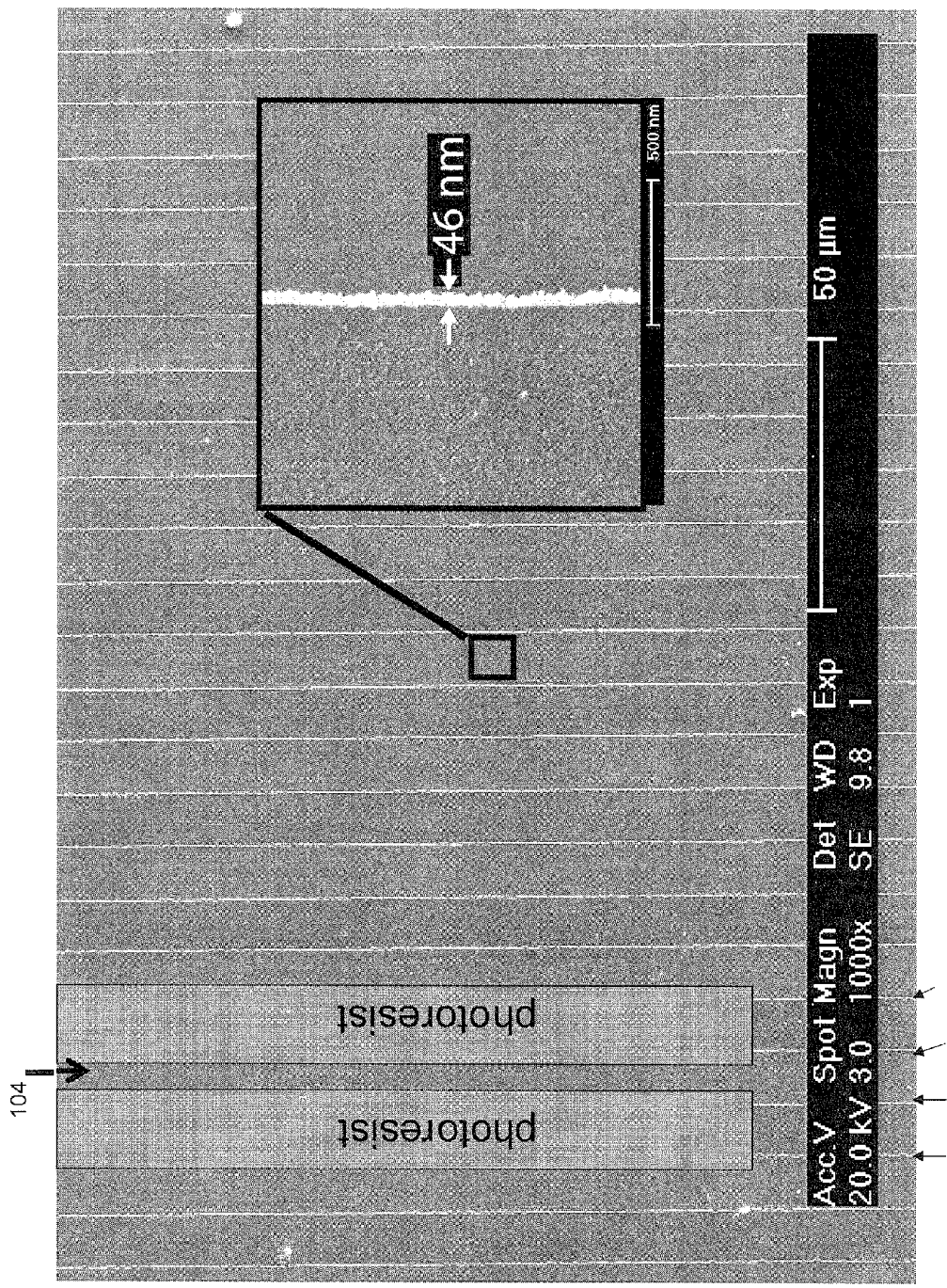
FIG. 7 is a top down image of a sensor having a plurality of electrode wires formed on the surface. Also illustrated are two layers of photoresist covering adjacent electrode wires. A magnified view of the electrode line or wire is also illustrated.

FIG. 7 is a top down micrograph image of a plurality of electrodes 92, 94 formed on a substrate. A magnified image of one of the plurality of electrodes 92, 94 is illustrated and has a width of 46 nm. As seen in FIG. 7, the location of the insulator layers 98 (e.g., photoresist) is shown above a pair of adjacent electrodes 92, 94. The photoresist layer 98 covers the adjacent, non-coupled electrode. In this regard, a channel 104 is formed in between every other pair of electrodes 92, 94.

Figure 8:
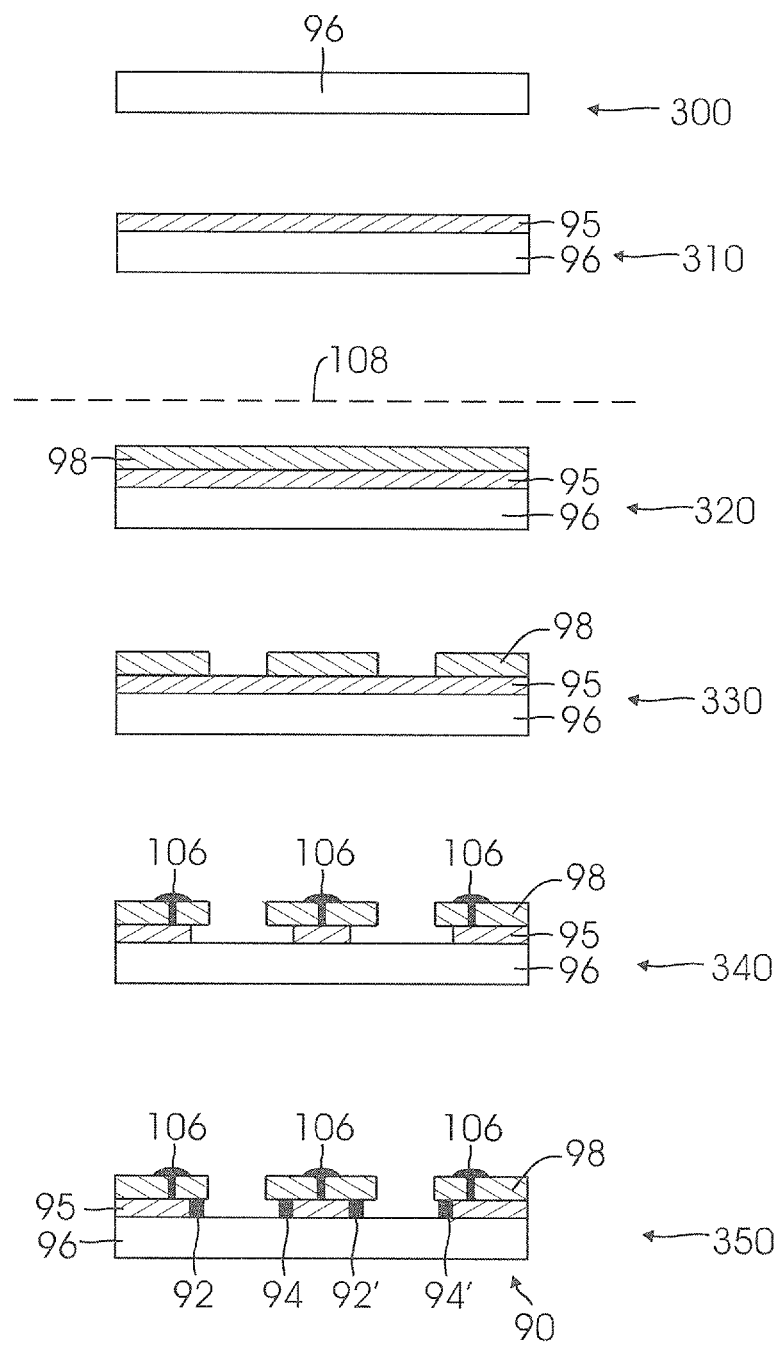
FIG. 8 illustrates a process of making a sensor having a plurality of electrode lines disposed on a surface of a substrate.

FIG. 8 illustrates a process of forming a sensor 90 of the type illustrated in FIGS. 6A, 6B and 7. Initially, in step 300, a substrate 96 is provided. For example, the substrate 96 may include a glass slide that is cleaned in NOCHROMIX for at least two days. Next, with reference to step 310, a layer of nickel 95 is deposited on a surface of the substrate 96. The nickel layer 95 may be deposited by, for instance, thermal evaporation of nickel metal. The thickness of the nickel layer 95 will be used to determine the height (H) of the electrodes 92, 94 described herein. In step 320 of FIG. 8, an insulator layer 98 is formed on top of the nickel layer 95. The insulator layer 320 may include, for example a photoresist. The photoresist may include SU-8 10 negative tone photoresist available from MICROCHEM of Newton, Mass. The SU-8 10 photoresist may be spin coated onto the nickel layer 95 in a two-step ramp process. First, the photoresist is spun on the nickel layer 95 for five seconds at a ramp rate of 100 rpm/sec (final speed is 500 rpm). Next, the photoresist is spun on for thirty seconds at a ramp rate of 300 rpm/sec (final speed is 2000 rpm).

The spin coated photoresist is then subject to a pre-bake process whereby the device is heated at 65° C. for two minutes then slowly ramped up to 95° C. The device then undergoes a "soft bake" at 95° C. for five minutes. After the soft bake process, the device is slowly cooled to room or ambient temperature. Next, with reference to step 320 of FIG. 8, a contact mask 108 is placed on the device with a quartz slide and is exposed to ultraviolet (UV) light for three minutes. UV light exposes the uncovered portions of the SU-8 10 photoresist. After UV light exposure, the now exposed device is placed into a developer solution for SU-8 10 for about three minutes to step 330. The developer solution may include, for instance, REMOVER PG available from MICROCHEM. The device is then rinsed with isopropyl alcohol (IPA) and dried with nitrogen.

The insulator layer 98 is then hard baked at 150° C. for about an hour. This process is accomplished by slowly ramping up the temperature from room temperature up to 150° C. then slowly ramped back down again to room temperature. Next, with reference to step 340, the nickel layer 95 is then chemically etched within 0.785 M nitric acid for about five minutes. The device is then rinsed with Millipore water (18.2 Mohm) and is dried with nitrogen. During this process, the etching of the nickel layer 95 underneath the photoresist layers 98 creates the recessed portions 100 caused by overhang of the un-reacted photoresist. As seen in step 340, portions of the insulator layer 98 may be scored or cut with a tool such as a razor blade to provide a conductive pathway for subsequent electrodeposition. Step 340 illustrates several such electrical contacts 106 formed within the remaining photoresist layer 98. The scored regions or openings may then be filled with an electrically conductive paste or paint (e.g., silver paste available from Ted Pella, Inc.) and allowed to dry to former electrical contact 106.

Next, with reference to step 350 of FIG. 8, the gold electrodes 92, 94 are electrodeposited by applying an electrical current to the nickel layer 95 via the electrical contacts 106. The channel portion 104 of the sensor 90 is loaded with a cyanide-free gold plating solution (Clean Earth Solutions Cyanide Free Gold Plating solution No. 45.216 of New Braunfels, Tex.). Gold is then deposited on the nickel layer 95 underneath the photoresist 98 by application of around −950 mV (verses a SCE electrode) for about one hundred seconds. The amount of time that gold is deposited will determine the width of the gold electrodes 92, 94. In one preferred embodiment, gold deposition should stop such that a ledge or overhang of photoresist remains over the newly formed electrodes 92, 94. This will minimize any potential leakage of the electrical field into the bulk solution (when loaded).

Figure 9:
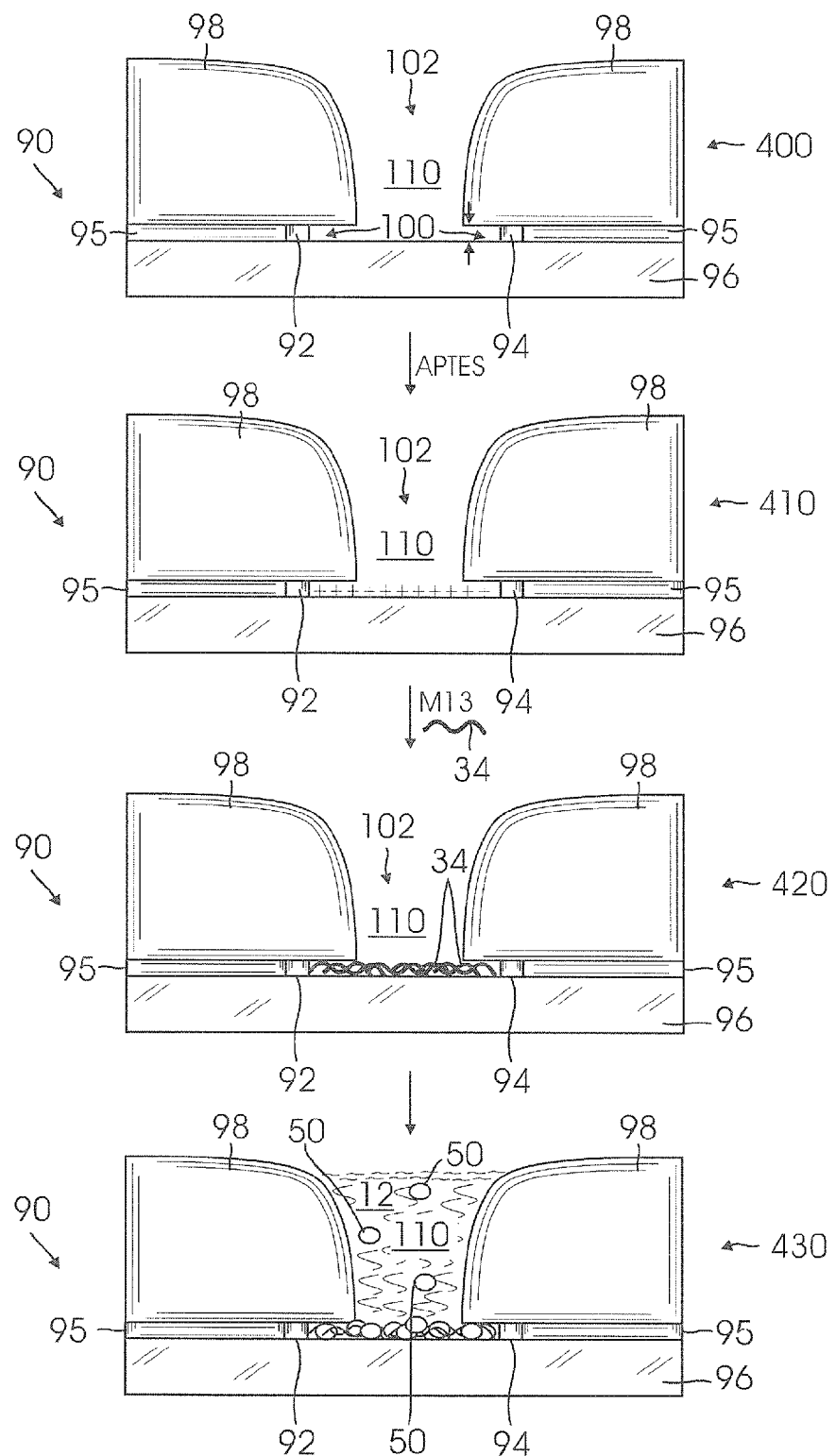
FIG. 9 illustrates a process of loading the sensor of FIGS. 6A, 6B, and 7-8 with a virus particles and subsequently exposing the same to a target or analyte that binds with the virus particles.

FIG. 9 illustrates a process of loading the sensor of FIG. 8 with virus particles 34 and then binding the same to target(s) 50. Step 400 comprises providing a sensor 90 as described above. In this state, the sensor 90 does not include any adhered virus particles 34. In order for the sensor 90 to detect and/or measure the concentration of a target 50, corresponding virus particles 34 that bind to the target(s) 50 of interest must be loaded onto the device. As seen in step 410 of FIG. 8 the surface of the substrate 96 located between the electrodes 92, 94 is chemically modified to electrostatically bind virus particles 34. To do this, the device of step 400 is first heated to around 100° C. in an oven for about twenty minutes. The heating is done to eliminate any moisture. The device is then removed from heat, cooled down and placed in a solution containing 2% (by volume) 3-amino-propyltriethoxy-silane (APES) in dry toluene for about thirty minutes. The APES treatment causes the surface of the substrate 96 located between the electrodes 92, 94 to be positively charged. The device is then washed or rinsed with toluene. The device may again be washed with an alcohol such as ethanol followed by a Nanopure water rinse.

Now referring to step 420 of FIG. 9, virus particles 34 (in FIG. 9 illustrated as M13 phage viruses) are then brought into contact with the positively charged surface of the substrate 96. For example, a portion of the device may be dipped or otherwise immersed in a solution containing the phage particles 34. An orbital shaker or the like may be used to promote mixing the solution. After binding of the phage particles 34 to the surface of the substrate 96 the device may be rinsed with a buffer solution such as PBF. Preferably, the device is kept in a wet state until use to preserve the integrity of the phage particles 34. Other types of virus particles 34, however, may be able to be stored in a dry state for some time. In this case, the device could be stored prior to use in a dry state. Referring now to step 430 in FIG. 9, a sample solution 12 containing target(s) 50 can then be placed into contact with the sensor 90. For example, sample solution 12 may be flowed or dropped into the channel 104. Targets 50 contained in the sample solution 12 may then bind with complementary virus particles 34 that are bound to the surface of the substrate 96.

After the sample solution 12 has come into contact with the sensor 90, the sensor 90 may be washed or rinsed with a rinsing agent (e.g., Tween-20/PBF buffer) to remove any un-bound materials from the phage-laden surface 96. The resistive impedance $Z_{Re}$ of the sensor 90 may then be measured using the impedance analyzer 40 as described herein. In one aspect of the invention, the measured resistive impedance $Z_{Re}$ may be enough to identify the presence or absence of a particular target 50. In this regard, there may be no need to subtract a baseline value of the measured resistive impedance when no targets 50 are present (e.g., measurements made just in buffer). Of course, in still other embodiments, the change in resistive impedance $Z_{Re}$ may be calculated and used to both detect the presence of a target 50 as well as the concentration of the target 50 in the sample solution 12.

Experiment #1

In a first experiment, a sensor of the type illustrated in FIG. 1 was developed and tested that used bacteriophage M13 that was covalently bound the surface of a gold electrode. M13 bacteriophage can selectively and simultaneously bind two biomolecules: an antibody (positive or p-Ab having a molecular weight of 150 kDa) and prostate-specific membrane antigen (PSMA having a molecular weight of 91.5 kDa). The M13 bacteriophage includes a phage-displayed peptide with the amino acid sequence CALCEFLG (SEQ. ID NO. 1). The peptide is fused to P8 (g8p), the major coat protein, and displayed on the surface of M13. A negative control antibody (n-Ab having a molecular weight of 150 kDa) was used to evaluate non-specific binding and biosensor selectivity.

Materials

All chemicals and solvents (>99% purity) were purchased from Fisher or Merck, and used as received, unless noted. DMF and ethanol were dried with 4 Å molecular sieves obtained from Alfa. The anti-M13 antibody (p-Ab) was purchased from Amersham Biosciences, and the anti-Flag® M2 (n-Ab) was purchased from Sigma. Nanopure water (resistance ~18 MΩ*cm, Barnstead Inc.) was used in all experiments.

With respect to buffers, PBF (5.7 mM $PO_4$, 140 mM NaF, pH 7.2) was filter sterilized through a 0.22 μm pore size membrane (Corning). For the wash buffer, 0.06% BSA and 0.035% Tween-20 (Sigma) were added to PBF. BSA (0.2%) in phosphate buffered sodium fluoride (pH 7.2) solution was used for blocking.

Virus Electrode Construction

Circular gold electrodes (3 mm in diameter) were polished with 1 μm and 0.25 μm diamond compound (Ted Pella) on microcloth (Buehler), and sonicated three times in Nanopure water for 3 minutes. Freshly prepared electrodes were rinsed with Nanopure water, dried with $N_2$, and incubated for at least 18 hours in a solution of N-hydroxysuccinimide thioctic ester (NHS-TE, 16.5 mM) dissolved in DMF. The NHS-TE modified electrode was stored in a desiccator. Phage with specific binding affinity for PSMA were selected from phage-displayed peptide libraries using techniques known to those skilled in the art. The amino acid sequence of the PSMA-specific peptide was CALCEFLG (SEQ. ID NO. 1). For reaction with the phage, a NHS-TE modified electrode was incubated in a phage solution (300 μl, 16 nM) and shaken for 1 hr by orbital shaker. Virus electrodes were rinsed 5 minutes with wash buffer and then 5 minutes with PBF. Virus electrodes were dipped in 300 μl 50% BSA solution and shaken another 40 minutes. The virus/BSA modified electrodes were rinsed for 5 minutes with Tween-20/PBF buffer and then 5 minutes with wash buffer.

Measurements with Virus Electrodes

For biosensor experiments, n-Ab, p-Ab, or PSMA (final concentration of 0.583 μM or as indicated) were diluted in wash buffer before the measurement. The virus electrode was immersed in the n-Ab, p-Ab or PSMA solution with shaking for 1 hour. The electrode was rinsed with wash buffer, before immersion for one minute in wash buffer for the following impedance measurement. All impedance measurements were carried out using a PARSTAT 2263 potentiostat (Princeton Applied Research, Inc.). These measurements employed an AC voltage amplitude of 10 mV over the frequency range from 1 MHz to 0.1 Hz, and at rest potential of the virus electrode. All cyclic voltammetry measurements were carried out in aqueous PBF using a saturated calomel electrode (SCE) as a reference electrode and a platinum counter electrode at a scanning rate of 20 $mV^{-1}$.

QCM Measurements

Au/Ti quartz disks (1 inch diameter) were prepared as described herein for the virus electrodes except that a fresh gold layer was first electrodeposited on the gold-covered quartz oscillator obtained from the manufacturer (Stanford Research Systems) by applying +0.7 V vs. SCE for 200 seconds in 10 mM $AuCl_3$ solution (pH 1). After gold deposition, the same procedure was employed for the attachment of viruses. This electrode was placed in a flow cell (shown in FIG. 11A) that provided for a radially symmetric delivery of solution to the circular-shaped QCM electrode surface. Mass measurements were made using a QCM 200 (Quartz Crystal Microbalance Digital Controller, 5 MHz Crystal Oscillator, Stanford Research Systems) with a flow rate of 10 μLmin$^{-1}$ obtained from a syringe pump. (Kd Scientific Inc.).

AFM Analysis

Intermittent contact mode atomic force microscopy (AFM) images were obtained in air at ambient pressure and humidity using a Park Scientific Instruments AutoProbe CP Research (now Veeco, Santa Barbara, Calif.) scanning probe microscope. The piezoelectric scanner was calibrated using a 1.0 μm grating in the xy directions and in the z direction using several conventional height standards. The tips were silicon (Ultrasharp cantilevers, model no. NSC11, MikroMasch). Topographs were obtained as 256×256 pixels and were flattened line-by-line and analyzed using AutoProbe image processing software supplied by the manufacturer of the AFM.

Fluorescence Analysis

Interdigitated electrodes with 2 μm gaps were made by photolithography in a clean room. The surface modification was similar to the preparation of the virus electrodes, except assembly took place in a PDMS flow cell with a 0.3 mm wide and 0.8 mm long channel. Fluorescently labeled anti-M13 antibody was added by syringe pump at the rate of 10 μl/min before rinsing with PBF-Tween and PBF solution for 10 minutes each. An Axioskop2 MAT microscope (Carl Zeiss Micromaging Inc.) equipped with an appropriate filter and Nikon Coolpix 5000 digital camera was used to visualize the electrode.

Results and Discussion

In this experiment, the biosensor consisted of a gold electrode covalently modified by M13 phage, which binds to an anti-M13 monoclonal antibody (p-Ab). For recognition of the prostate cancer marker, Prostate Specific Membrane Antigen (PSMA), phage with high affinity for PSMA were isolated from selections of a ~5×10$^{11}$ diversity peptide library. This PSMA-phage binds both PSMA and p-Ab and, like M13 phage, fails to bind negative control antibody (n-Ab, anti-His tag monoclonal Ab). Phage and antibody were attached and measured in PBF-tween-BSA solutions, with the exception of the QCM experiments that omitted BSA to reduce background. This buffer provides a realistic assessment of the potential for this device to perform physiological measurements, as it includes a high salt concentration (I>140 mM) and pH 7.2.

Preparation of a pinhole-free, covalent virus surface proved critical for reliable electrochemical measurements. The gold surface was first polished and then activated by briefly electrodepositing a small amount of fresh gold. As shown schematically in FIG. 5, phage particles 34 were anchored to the gold electrode 18 via a self-assembled monolayer (SAM) of thioctyl NHS ester. This SAM required ~18 hours to assemble from a dry DMF solution of the NHS-activated ester and, after reaction with the phage, produced a dense, electrically resistive covalent virus layer. The electrode was imaged by non-contact atomic force microscopy (NC-AFM) and the clean gold surface was characterized by a RMS roughness of <1 nm with 10 μm diameter gold grains delineated by grain boundaries as illustrated in FIG. 10A. After covalent virus modification, NC-AFM imaging shown in FIG. 10B shows a striated surface with a roughness of 2-3 nm. Because individual M13 phage particles are ~6-8 nm in diameter and approximately 1 μm in length, the striations observed in FIG. 10B are consistent with the presence of aligned bundles of phage M13 particles on the gold surface. In conjunction with adsorbed BSA, this covalent virus layer sharply increased the resistance of the electrode surface with the largest increase observed at lower frequencies as shown by FIG. 10C.

With reference to FIG. 10D, the covalent virus surface layer, after exposure to BSA, was dense enough to completely suppress the electrochemical signatures of the underlying gold surfaces (compare upper virus electrode to bare gold trace). The cyclic voltammogram for a bare gold electrode in PBF buffer illustrated in FIG. 10D shows three electrochemical reactions including: (1) a reversible oxidation of the gold (at 0.5 V), (2) reduction of the resultant gold oxide (at 0.2 V), and (3) reduction of $H^+$ to form $H_2$ (at 0.0 V). After covalent virus modification and BSA/p-Ab treatment, none of these three reactions are observed (virus electrode in FIG. 10D) indicating that the gold electrode is insulated from direct contact with the electrolyte solution. If the potential of this electrode is, however, scanned repeatedly to +1.0 V, the SAM is oxidatively desorbed, thereby releasing the virus and p-Ab from the gold surface. As the SAM desorption proceeds over the course of ten voltammetric scans (shown by opposing arrows of lowermost scan in FIG. 10D), current peaks characteristic of bare gold emerge. The biosensor selectivity for p-Ab versus n-Ab and PSMA that we demonstrate next required covalent virus surfaces with this strong passivation of the gold surface.

To guide development of the virus electrode, two independent methods were used to evaluate the functioning of the covalent virus surface. First, quartz crystal microbalance (QCM) gravimetry permitted mass changes at the covalent virus surface to be directly measured during the exposure of these surfaces to p-Ab and n-Ab. Results of this are illustrated in FIG. 11A. QCM measurements revealed that virus electrodes rapidly and irreversibly bind p-Ab but do not bind n-Ab to any measurable extent. Omission of the phage, followed by addition of buffer and BSA, resulted in a surface that was incapable of binding fluorescently-labeled p-Ab. This can be seen in FIG. 11C which illustrates no binding. As expected, the covalent virus surface recognized and bound the fluorescently labeled p-Ab as is shown in FIG. 11D. The fluorescin-labeled p-Ab is clearly seen in FIG. 11D positioned on the patterned gold electrodes illustrated in FIG. 11B.

Figure 12A:
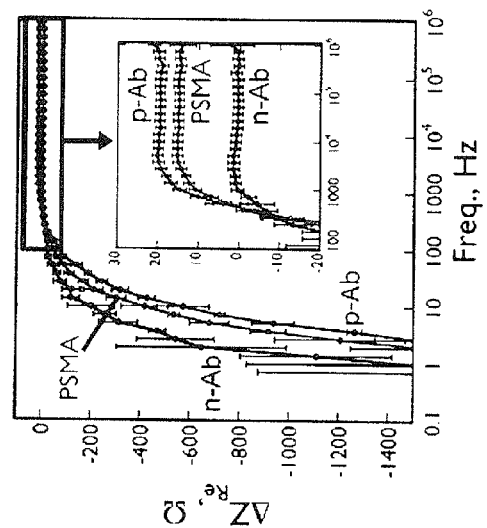
FIG. 12A illustrates a graph of the change capacitive impedance $\Delta Z_{Im}$ as a function of applied frequency for a 3 mm diameter gold electrode sensor bound with phage. Graphs are illustrated during conditions when the electrode was exposed to n-Ab, PSMA, and p-Ab. Also shown is an expanded view of the region between about 100 Hz to 10$^6$ Hz with corresponding error bars.
Figure 12B:
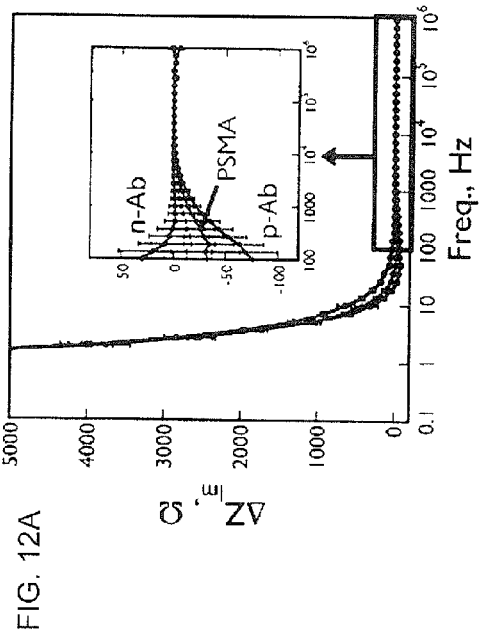
FIG. 12B illustrates a graph of the change resistive impedance $\Delta Z_{Re}$ as a function of applied frequency for a 3 mm diameter gold electrode sensor bound with phage. Graphs are illustrated during conditions when the electrode was exposed to n-Ab, PSMA, and p-Ab. Also shown is an expanded view of the region between about 100 Hz to 10$^6$ Hz with corresponding error bars.
Figure 12C:
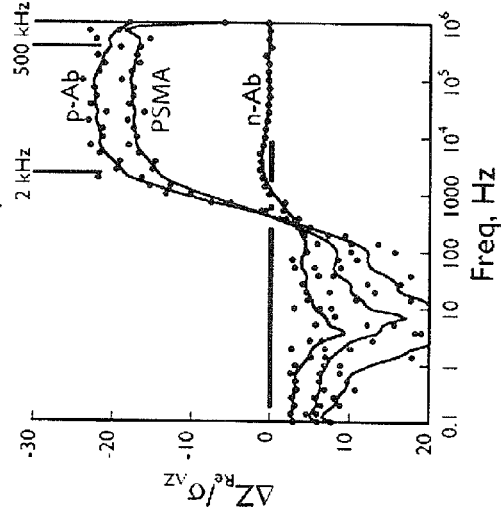
FIG. 12C illustrates a graph of the signal-to-noise ratio $\Delta Z_{Im}/\sigma_{\Delta z}$ for the change in capacitive impedance $\Delta Z_{Im}$ of the gold electrode.

Electrochemical impedance spectroscopy evaluated performance by the virus electrode in response to exposure to n-Ab, PSMA, and p-Ab. FIGS. 12A-12D illustrate the impedance change (both capacitive and resistive) as a function of applied frequency. Also illustrated (FIGS. 12C and 12D) are the signal-to-noise ratios associated with these particular measurements. These experiments explored two modes of detection. First, the virus electrode was exposed to analyte for 1 hour, rinsed with wash buffer, and then transferred to wash buffer for impedance measurement. In FIGS. 12A and 12B, signal is defined as the change in impedance which is either capacitive, $\Delta Z_{Im}$ (FIG. 12A) or resistive, $\Delta Z_{Re}$ (FIG. 12B) relative to the initial impedance of the covalent virus surface, following BSA treatment (i.e., virus electrode in buffer). In the frequency range from 100 Hz to direct current (dc), both $\Delta Z_{Im}$ and $\Delta Z_{Re}$ increased exponentially with the reduction in frequency. While the relatively large signal amplitudes seen at very low frequencies has been seen as a rationale for employing frequencies below 1 Hz in biosensors, these results find that the measurement-to-measurement variability of $\Delta Z_{Im}$ and $\Delta Z_{Re}$, as measured by the standard deviation obtained for replicate measurements, $\sigma_{\Delta Z}$ (plotted as error bars in FIGS. 12A and 12B), increased in parallel with $\Delta Z$ for both $\Delta Z_{Im}$ and $\Delta Z_{Re}$. Thus, low frequencies provide a large signal, but unfortunately a proportionally larger noise background. However, between 2 kHz and 500 kHz, $\Delta Z_{Im}$ becomes small as shown in FIG. 12A, but $\Delta Z_{Re}$ is readily measurable with a positive signal for both p-Ab and PSMA, and near zero signal for n-Ab as illustrated in FIG. 12B.

The positive value of $\Delta Z_{Re}$ over this frequency range means that the analyte or target-bound state of the virus electrode has a higher resistance than the initial state of the electrode before exposure to analyte. This higher resistance may derive from the formation of a bound analyte layer situated atop the virus electrode. It is believed that these bound analyte molecules can both displace electrolyte, and impede ion transport to the electrode surface by physically blocking it.

Figure 12D:
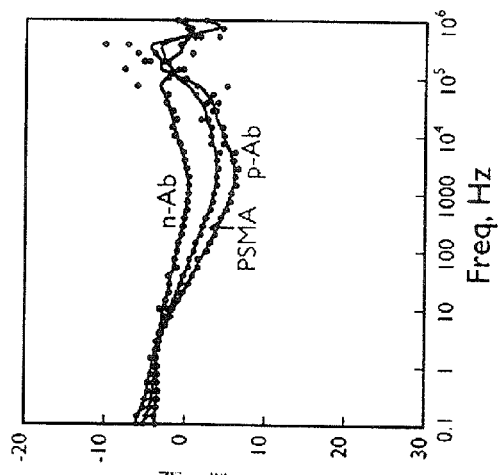
FIG. 12D illustrates a graph of the signal-to-noise ratio $\Delta Z_{Re}/\sigma_{\Delta Z}$ for the change in resistive impedance $\Delta Z_{Re}$ of the gold electrode. In addition, FIG. 12D highlights the region between 2 kHz and 500 kHz where a relatively high signal-to-noise ratio is observed for both PSMA and p-Ab.

The data of FIGS. 12A and 12B suggest that the ratio between $\Delta Z$ and $\sigma_{\Delta Z}$ at each frequency may provide a better figure-of-merit than $\Delta Z$. When $\Delta Z/\sigma_{\Delta Z}$, or the signal-to-noise ratio, is plotted versus frequency for both capacitive and resistive channels (FIGS. 12C and 12D, respectively), it is apparent that the highest values (i.e., those with the highest signal-to-noise ratios) are obtained in the resistive channel within the frequency range from about 2 kHz to about 500 kHz. Here, $\Delta Z_{Re}/\sigma_{\Delta Z}=16$ for PSMA and $\Delta Z_{Re}/\sigma_{\Delta Z}=20$ for p-Ab (FIG. 12D). Furthermore, measured $\Delta Z_{Re}/\sigma_{\Delta Z}$ values remained virtually invariant over this frequency range (e.g., about 2 kHz to about 500 kHz).

Figure 13B:
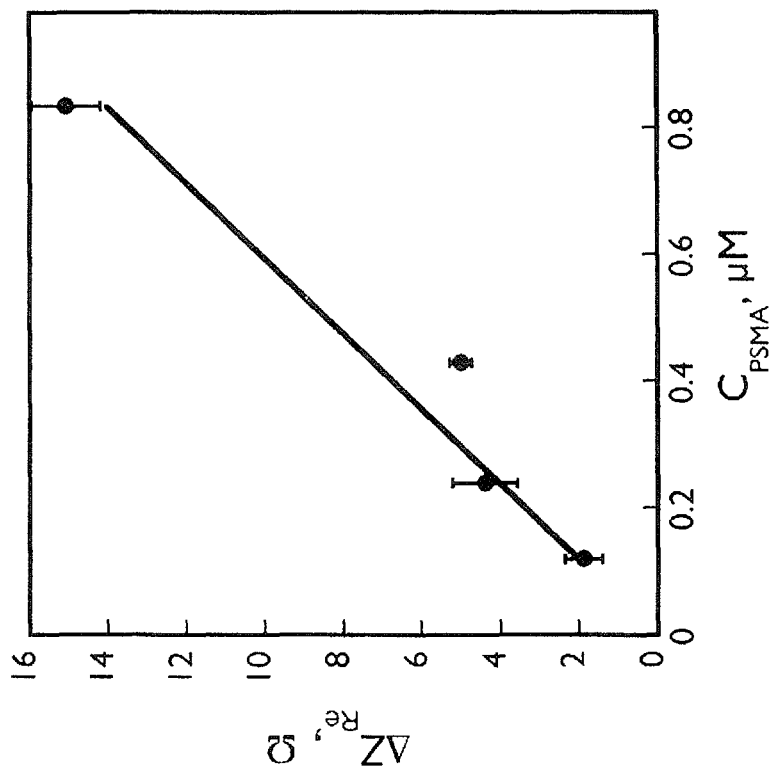
FIG. 13B illustrate a calibration curve for PSMA detection using a gold disk electrode. Each data point represents the average change in resistive impedance $\Delta Z_{Re}$ for four separate electrodes exposed to varying concentrations of PSMA.
Figure 13A:
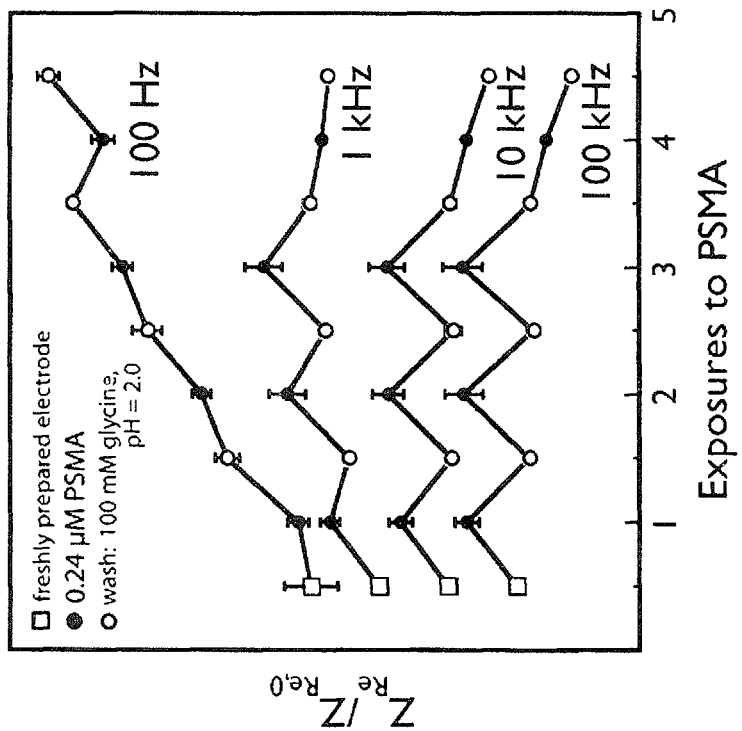
FIG. 13A illustrates a graph of the resistive impedance $Z_{Re}$ of the gold electrode after exposure to 0.24 µM PSMA and subsequent rinsing with aqueous 100 mM glycine at pH 2.0. Measurements are shown at four frequencies, 100 Hz, 1 kHz, 10 kHz, and 100 kHz.

FIG. 13A illustrates the measuring the frequency-dependant value of $Z_{Re}$ as a virus electrode was first exposed to PSMA and then subsequently rinsed to release PSMA from the sensor surface. As seen in FIG. 13A, only at 10 kHz and 100 kHz is the impedance of the freshly prepared virus electrode recovered after this rinsing operation. At these frequencies, the resistance of the high $Z_{Re}$ state associated with bound PSMA and the low $Z_{Re}$ state associated with a clean sensor surface are reproduced for three successive exposure/rinse cycles prior to failure of the sensor upon the fourth exposure to PSMA. Using 10 kHz, the dependence of $\Delta Z_{Re}$ on the concentration of PSMA can be measured. For example, FIG. 13B illustrates a calibration curve of four separate sensors 14 each exposed to a different concentration of PSMA. Based on the calibration curve of FIG. 13B, these data permit a limit-of-detection for PSMA of approximately 120 nM to be estimated using the sensor 14, which is a value comparable to levels observed in the seminal fluid of healthy men. During operational use of the sensors 14, 90, the data from the calibration curve may be loaded into the impedance analyzer 40 and/or the computer 42 to determine the concentration of the target(s) 50 in the sample or test solution 12. For example, once the $\Delta Z_{Re}$ has been measured, the corresponding concentration can then be determined based on the calibration curve. This may be accomplished via a look-up-table, database, or software that contains the calibration curve for the particular target 50 of interest. In one aspect of the invention, when there is a plurality of electrodes 92, 94 like in sensor 90, there may be a separate calibration curve for each of the targets 50 that correspond to the virus particles 34 loaded onto the sensor 90.

Experiment #2

Figure 14:
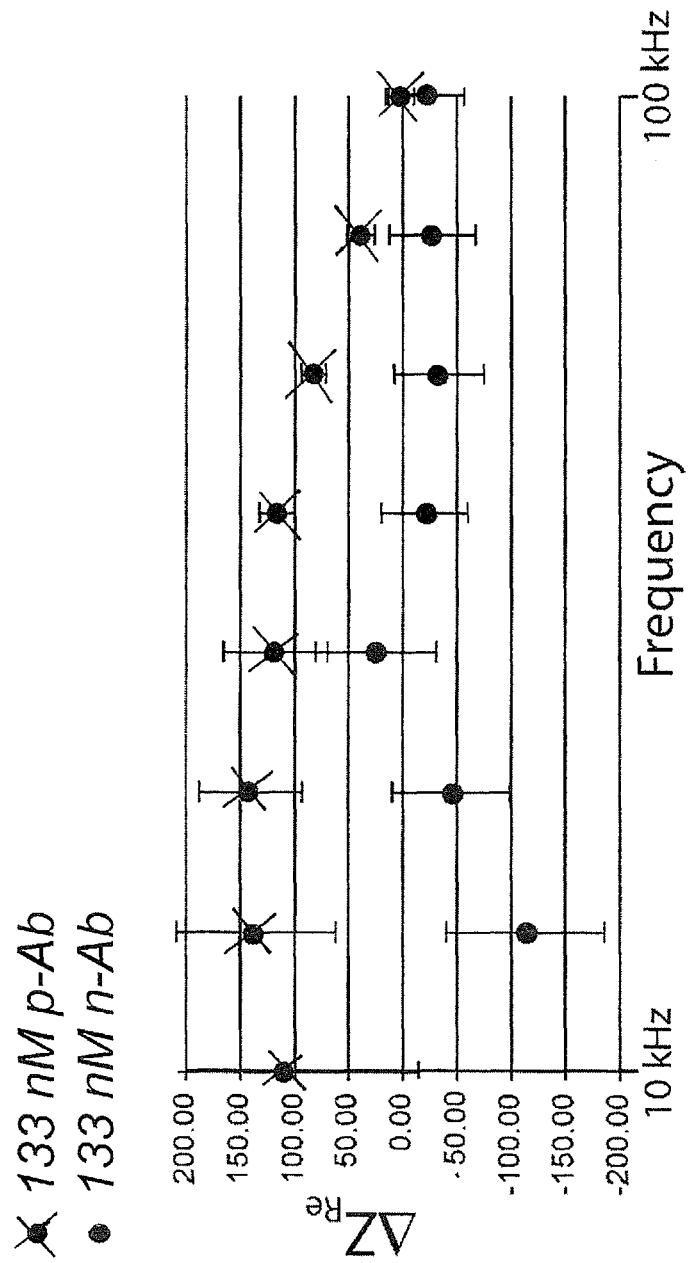
FIG. 14 illustrates the measured $\Delta Z_{Re}$ obtained using a sensor of the type illustrated in FIGS. 6A and 6B that was loaded with 133 nM of n-Ab and 133 nM of p-Ab. Measurements were taken over a frequency range of 10 kHz to 100 kHz.

In a second experiment, multiple sensors 90 of the type illustrated in FIGS. 6A, 6B, and 7-9 were exposed to 133 nM n-Ab and 133 nM p-Ab. Using an impedance analyzer 40, $\Delta Z_{Re}$ was calculated over a range of applied frequencies ranging from 10 kHz to 100 kHz. FIG. 14 illustrates a graph of $\Delta Z_{Re}$ as a function of the applied frequency for both n-Ab and p-Ab. As seen in FIG. 14, a positive $\Delta Z_{Re}$ value is obtained in the frequency range of 10 kHz to about 90 kHz. Consequently, the sensor 90 is able to detect the presence of p-Ab in concentrations as low as 133 nM. In this particular experiment, the electrodes 92, 94 had a height of 40 nm and were separated by 11 mm. It is believed that the sensitivity of the sensor 90 may be increased by reducing the separation between adjacent electrodes 92, 94, thereby enabling detection of even lower concentrations of p-Ab.

There are numerous applications for the sensors 14, 90 described herein. For example, the sensors 14, 90 may be used for non-invasive cancer diagnostics and screening. In addition, because sensors 14, 90 may be tailored for virtually any target molecule, the sensors 14, 90 may also have application in other diagnostic applications. Moreover, because of the compact and rugged nature of the sensors 14, 90, they may be particularly well suited to provide sensitive, direct assays for environmental monitoring and detection applications. For instance, the sensors 14, 90 are able to operate for several hours in the presence of high ionic strength buffers. Finally, the sensors 14, 90 may also be used in biodefense and other applications.

While embodiments of the present invention have been shown and described, various modifications may be made without departing from the scope of the present invention. The invention, therefore, should not be limited, except to the following claims, and their equivalents.

What is claimed is:

1. A biosensor comprising:
   an electrically conductive gold electrode operatively coupled to an impedance analyzer for measuring the change in the resistive impedance $\Delta Z_{Re}$ of the electrode;
   a self-assembled monolayer chemically bonded to a surface of the electrically conductive gold electrode via a thiol-gold bond formed between N-hydroxysuccinimide thioctic ester and the gold electrode; and
   a plurality of phage virus particles covalently bound to the self-assembled monolayer.

2. The biosensor of claim 1, further comprising one or more macromolecules disposed in the self-assembled monolayer.

3. The biosensor of claim 2, wherein the macromolecule comprises bovine serum albumin (BSA) disposed in the self-assembled monolayer.

4. The biosensor of claim 1, wherein the plurality of phage particles comprise bacteriophage M13.

5. The biosensor of claim 1, wherein the plurality of phage particles selectively bind to prostate specific membrane antigen (PSMA).

6. The biosensor of claim 1, further comprising a processor operatively connected to the impedance analyzer for calculating an analyte concentration based at least in part on the measured change in resistive impedance $\Delta Z_{Re}$.

7. The biosensor of claim 1, wherein substantially the entire self-assembled monolayer is pinhole free.

8. The biosensor of claim 1, wherein the impedance analyzer is operatively coupled to the electrically conductive gold electrode so as to apply an alternating current within the frequency range of about 2 kHz to about 500 kHz.

9. A system for detecting the presence of an analyte in a sample comprising:
   an electrically conductive gold electrode operatively coupled to an impedance analyzer for measuring the change in the resistive impedance $\Delta Z_{Re}$ of the gold electrode in response to an applied alternating current;
   a self-assembled monolayer chemically bonded to a surface of the electrically conductive gold electrode via a thiol-gold bond formed between N-hydroxysuccinimide thioctic ester and the gold electrode;
   a plurality of phage virus particles covalently bound to the self-assembled monolayer; and
   at least one processor operatively coupled to the impedance analyzer for comparing the change in the measured resistive impedance $\Delta Z_{Re}$ with one or more pre-set values, the at least one processor configured for outputting a signal indicative of analyte detection based at least in part on the comparison.

10. The system of claim 9, wherein the electrically conductive gold electrode is disposed in a flow cell.

11. The system of claim 9, wherein the at least one processor is configured for outputting a signal indicative of the analyte concentration based at least in part on the comparison.

12. The system of claim 9, wherein the electrically conductive gold electrode comprises an array of electrodes.

13. The system of claim 9, wherein the electrically conductive gold electrode is disposed in a probe.

\* \* \* \* \*

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Cys Ala Leu Cys Glu Phe Leu Gly
1               5
```